US00PP34427P2

(12) United States Plant Patent
Kobayashi

(10) Patent No.: US PP34,427 P2
(45) Date of Patent: Jul. 19, 2022

(54) **NEW GUINEA *IMPATIENS* PLANT NAMED 'DONGIPETORSTA 21'**

(50) Latin Name: *Impatiens hawkeri*
Varietal Denomination: 'Dongipetorsta 21'

(71) Applicant: DUMMEN GROUP B.V., De Lier (NL)

(72) Inventor: Ruth Kobayashi, Carlsbad, CA (US)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 17/571,194

(22) Filed: Jan. 7, 2022

(51) Int. Cl.
*A01H 5/02* (2018.01)
*A01H 6/16* (2018.01)

(52) U.S. Cl.
USPC ..... Plt./318.1
CPC ..... *A01H 6/165* (2018.05)

(58) Field of Classification Search
USPC ..... Plt./318.1
CPC ..... A01H 6/165
See application file for complete search history.

(56) References Cited

PUBLICATIONS

CPVO hit showing UPOV QZ PBR 2020/2730, filed Oct. 29, 2020.*

* cited by examiner

*Primary Examiner* — Anne Marie Grunberg
(74) *Attorney, Agent, or Firm* — C. Anne Whealy

(57) ABSTRACT

A new and distinct cultivar of *Impatiens* plant named 'Dongipetorsta 21' characterized by its upright to outwardly spreading and mounding plant habit; moderately vigorous to vigorous growth habit; freely branching habit; dark green-colored leaves; freely and early flowering habit; medium-sized orangish red and pale purplish pink bi-colored flowers; and good garden performance.

2 Drawing Sheets

Figure 1:
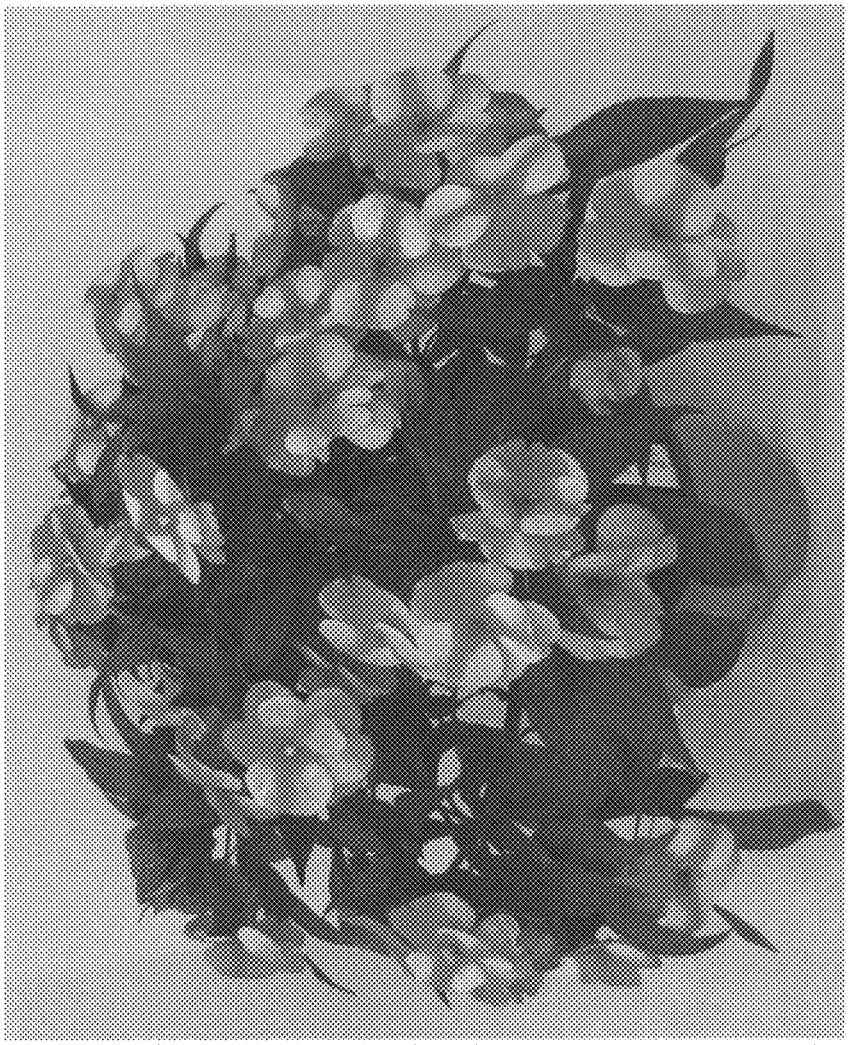

Botanical designation: *Impatiens hawkeri.*
Cultivar denomination: 'DONGIPETORSTA 21'.

STATEMENT REGARDING PRIOR DISCLOSURES BY INVENTOR & APPLICANT/ASSIGNEE

An European Community Plant Breeder's Rights application for the instant plant was filed by the Applicant on Oct. 29, 2020, application number 2020/2730. Foreign priority is not claimed to this application.

The Inventor and Applicant assert that no publications nor advertisements relating to sales, offers for sale or public distribution occurred more than one year prior to the effective filing date of this application. Any information about the claimed plant would have been obtained from a direct or indirect disclosure from the Inventor and/or Applicant. Inventor and Applicant claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of New Guinea *Impatiens* plant, botanically known as *Impatiens hawkeri* and hereinafter referred to by the name 'Dongipetorsta 21'.

The new *Impatiens* plant is a product of a planned breeding program conducted by the Inventor in Koka, Ethiopia and Encinitas, Calif. The objective of the breeding program is to create new freely-branching, early and freely flowering New Guinea *Impatiens* plants with large attractive flowers and good garden performance.

The new *Impatiens* plant originated from a cross-pollination made by the Inventor in November, 2016 in Koka, Ethiopia of a proprietary selection of *Impatiens hawkeri* identified as code number NN14-516311-006, not patented, as the female, or seed, parent with a proprietary selection of *Impatiens hawkeri* identified as code number NN12-002628-003, not patented, as the male, or pollen, parent. The new *Impatiens* plant was discovered and selected by the Inventor as a single flowering plant from within the progeny of the stated cross-pollination in a controlled greenhouse environment in Encinitas, Calif. in April, 2017.

Asexual reproduction of the new *Impatiens* plant by terminal vegetative cuttings in a controlled greenhouse environment in Encinitas, Calif. since June, 2017 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Dongipetorsta 21'. These characteristics in combination distinguish 'Dongipetorsta 21' as a new and distinct *Impatiens* plant:

1. Upright to outwardly spreading and mounding plant habit.
2. Moderately vigorous to vigorous growth habit.
3. Freely branching habit.
4. Dark green-colored leaves.
5. Freely and early flowering habit.
6. Medium-sized orangish red and pale purplish pink bi-colored flowers.
7. Good garden performance.

Plants of the new *Impatiens* can be compared to plants of the female parent selection. Plants of the new *Impatiens* differ primarily from plants of the female parent selection in the following characteristics:

1. Plants of the new *Impatiens* are more outwardly spreading and mounding than and not as upright as plants of the female parent selection.
2. Flowers of plants of the new *Impatiens* are orangish red and pale purplish pink bi-colored whereas flowers of plants of the female parent selection are bright red and light pink-bi-colored.

Plants of the new *Impatiens* can be compared to plants of the male parent selection. Plants of the new *Impatiens* differ primarily from plants of the male parent selection in the following characteristics:

1. Plants of the new *Impatiens* are not as vigorous as plants of the male parent selection.
2. Flowers of plants of the new *Impatiens* are flatter than and not as cupped as flowers of plants of the male parent selection.
3. Flowers of plants of the new *Impatiens* are orangish red and pale purplish pink bi-colored whereas flowers of plants of the male parent selection are bright red and light pink-bi-colored.

Plants of the new *Impatiens* can be compared to plants of *Impatiens hawkeri* 'Duepetrest', disclosed in U.S. Plant Pat. No. 11,375. In side-by-side comparisons, plants of the new *Impatiens* differ primarily from plants of 'Duepetrest' in the following characteristics:

1. Plants of the new *Impatiens* are more vigorous than plants of 'Duepetrest'.
2. Plants of the new *Impatiens* have larger flowers than plants of 'Duepetrest'.
3. Flowers of plants of the new *Impatiens* are orangish red and pale purplish pink bi-colored whereas flowers of plants of 'Duepetrest' are soft red and light lavender bi-colored.

Plants of the new *Impatiens* can also be compared to plants of *Impatiens hawkeri* 'Tamar Purple Bicolor', disclosed in U.S. Plant Pat. No. 15,462. In side-by-side comparisons, plants of the new *Impatiens* differ primarily from plants of 'Tamar Purple Bicolor' in the following characteristics:

1. Plants of the new *Impatiens* flower about one week earlier than plants of 'Tamar Purple Bicolor'.
2. Plants of the new *Impatiens* flower have slightly smaller flowers than plants of 'Tamar Purple Bicolor'.
3. Flowers of plants of the new *Impatiens* are orangish red and pale purplish pink bi-colored whereas flowers of plants of 'Tamar Purple Bicolor' are red purple in color with a darker central band.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph on the first sheet (FIG. 1) is a side perspective view of a typical flowering plant of 'Dongipetorsta 21' grown in a container.

Figure 2:
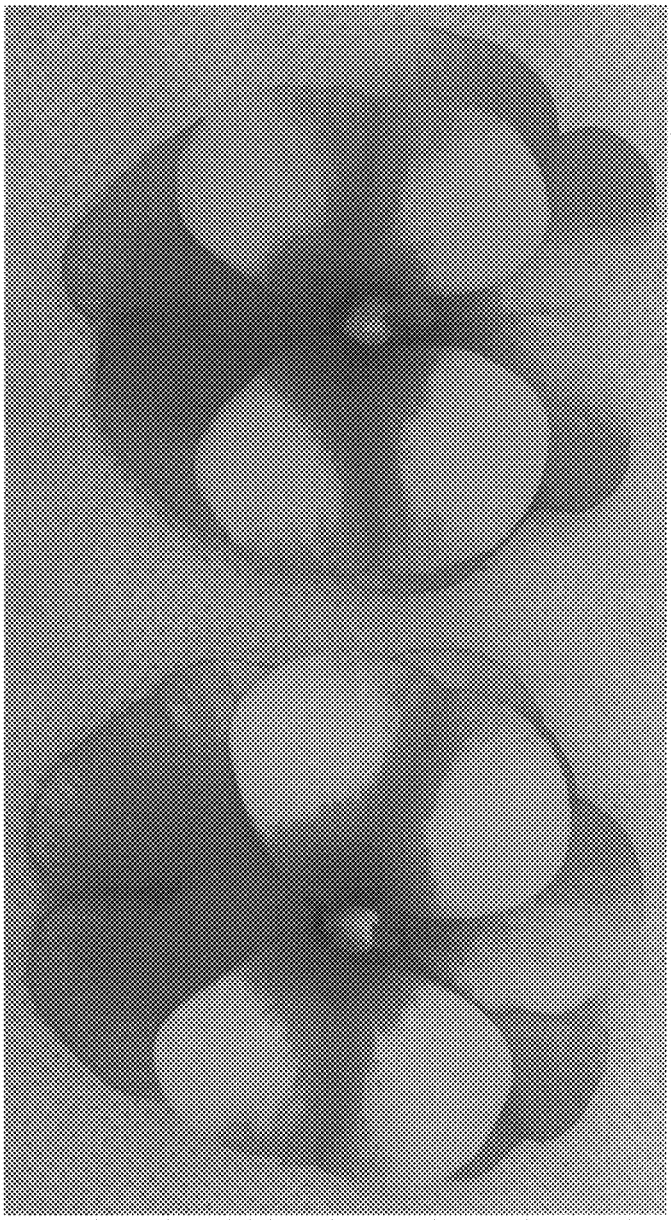

The photograph on the second sheet (FIG. 2) is a close-up view of typical flowers of 'Dongipetorsta 21'.

DETAILED BOTANICAL DESCRIPTION

The aforementioned photographs and following observations, measurements and values describe plants grown during the summer and autumn in winter and early spring in 16.5-cm containers in a polyethylene-covered greenhouse in Encinitas, Calif. and under cultural practices typical of commercial New Guinea *Impatiens* production. During the production of the plants, day temperatures averaged 25° C., night temperatures averaged 18° C. and light levels ranged from 4,000 to 4,500 lux. Plants were 13 weeks old when the photographs were taken and 17 weeks old when the description was taken. In the following description, color references are made to The Royal Horticultural Society Colour Chart, 2015 Edition, except where general terms of ordinary dictionary significance are used.

Botanical classification: *Impatiens hawkeri* 'Dongipetorsta 21'.

Parentage:

*Female, or seed, parent*.—Proprietary selection of *Impatiens hawkeri* identified as code number NN14-516311-006, not patented.

*Male, or pollen, parent*.—Proprietary selection of *Impatiens hawkeri* identified as code number NN12-002628-003, not patented.

Propagation:

*Type*.—By terminal vegetative cuttings.

*Time to initiate roots, summer and winter*.—About five to seven days at temperatures about 27° C. and night temperatures about 20° C.

*Time to produce a rooted young plant, summer and winter*.—About three weeks at day temperatures about 27° C. and night temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Upright to outwardly spreading and mounding plant habit; broad inverted triangle in overall shape; freely branching habit with lateral branches potentially developing at every node; moderately vigorous to vigorous growth habit and moderate growth rate.

*Plant height*.—About 27 cm.

*Plant diameter*.—About 52 cm.

Lateral branch description:

*Length*.—About 22 cm.

*Diameter*.—About 1.5 cm.

*Internode length*.—About 5.75 cm.

*Strength*.—Strong, stout; flexible.

*Aspect*.—Initially upright to outwardly spreading to almost horizontal.

*Texture and luster*.—Smooth, glabrous; glossy.

*Color, developing*.—Close to 148A heavily overlain with close to 187A.

*Color, fully developed*.—Close to 187A to 187B.

Leaf description:

*Arrangement*.—Typically in whorls; simple.

*Length*.—About 10 cm.

*Width*.—About 4.5 cm.

*Shape*.—Lanceolate to elliptic.

*Apex*.—Acuminate.

*Base*.—Cuneate.

*Margin*.—Serrate with ciliation.

*Texture and luster, upper surface*.—Smooth, glabrous; glossy.

*Texture and luster, lower surface*.—Smooth, glabrous; semi-glossy.

*Venation pattern*.—Pinnate; arcuate.

*Color*.—Developing leaves, upper surface: More green than 147A. Developing leaves, lower surface: Close to 187B. Fully expanded leaves, upper surface: Darker green than 147A; midvein, close to 187B and lateral venation, darker green than 147A. Fully expanded leaves, lower surface: Close to 187A to 187B; venation, close to 187A to 187B.

*Petiole length*.—About 5 cm.

*Petiole diameter*.—About 4 mm.

*Petiole texture and luster, upper and lower surfaces*.—Smooth, glabrous; glossy.

*Petiole color, upper surface*.—Close to 187B to 187C.

*Petiole color, lower surface*.—Close to 187B.

Flower description:

*Flower type and flowering habit*.—Single, medium-sized and rounded rectangular axillary flowers; freely flowering habit, typically about seven to nine open flowers and flower buds per lateral branch; flowers positioned above and beyond the foliar plane, flowers typically face mostly upright to outwardly.

*Flower longevity*.—Flowers typically last about four to seven days on the plant under greenhouse conditions; petals self-cleaning, gynoecium persistent.

*Fragrance*.—None detected.

*Natural flowering season*.—Year-round under greenhouse conditions; in the garden, flowering from spring until fall in California; early flowering habit, plants typically begin flowering about ten weeks after planting.

*Flower buds*.—Length: About 1.3 cm. Diameter: About 1 cm. Shape: Ovoid. Texture and luster: Smooth, glabrous; glossy. Color: Petals, close to 46A; sepals, close to 148A variably overlain with close to 187A to 187B.

*Flower diameter*.—About 5 cm by 6 cm.

*Flower depth*.—About 1.5 cm.

*Petals*.—Quantity and arrangement: Five per flower in a single whorl. Length, banner petal: About 3 cm. Length, lateral petals: About 2.7 cm. Length, lower petals: About 2.75 cm. Width, banner petal: About 3.75 cm. Width, lateral petals: About 3.25 cm. Width, lower petals: About 3.4 cm. Shape, banner petal: Broadly cordate. Shape, lateral and lower petals: Cordate to broadly cordate. Apex, all petals: Cordate. Base, all petals: Cuneate. Margin, all petals: Mostly entire with occasional and random indentations. Texture and luster, all petals, upper surface: Smooth, glabrous; velvety; matte; iridescent. Texture and luster, all petals, lower surface: Smooth, glabrous; matte; iridescent. Color, all petals: When opening and fully opened, upper surface: Centers, close to 44A; towards the margins, close to 55C to 55D; venation, similar to lamina; color does not change with development. When opening and fully opened, lower surface: Centers, close to 44C to 44D; towards the margins, close to 44D; venation, similar to lamina; color does not change with development.

*Sepals*.—Quantity and arrangement: Three in a single whorl; one modified into an elongated spur. Lateral sepal length: About 1 cm. Lateral sepal width: About 4 mm. Spur sepal length: About 1.4 cm. Spur sepal width: About 1 cm. Sepal shape: Elongated deltoid. Sepal apex: Cuspidate. Sepal base: Truncate. Sepal margin: Entire. Sepal texture and luster, upper surface: Smooth, glabrous; slightly glossy. Sepal texture and luster, lower surface: Smooth, glabrous; semi-glossy. Lateral sepal color, upper surface: Close to 157A to 157B. Lateral sepal color, lower surface: Close to 178A to 178B. Spur sepal color, upper surface: Close to 56A. Spur sepal color, lower surface: Close to 55B. Spur length: About 3.25 cm. Spur diameter: At flower, about 2.5 mm; at apex, less than 1 mm. Spur texture and luster: Smooth, glabrous; somewhat glossy. Spur color: Close to 55B; distally, close to 145A to 145B.

*Peduncles*.—Length: About 4.75 cm. Diameter: About 2.5 mm. Angle: About 45° from stem axis. Strength: Strong; flexible. Texture and luster: Smooth, glabrous; semi-glossy. Color: Close to 146C.

*Reproductive organs*.—Stamens: Quantity: Five fused at anthers; filaments free. Anther size: About 4 mm by 1 mm. Anther shape: Oblong. Anther color: Close to 11D. Pollen amount: If present, scarce. Pollen color: Close to 11D. Pistils: Quantity per flower: One. Pistil length: About 4 mm. Stigma shape: Crested. Stigma color: Close to 144A. Style color: Close to 144A. Ovary color: Close to 144A.

*Seeds and fruits*.—To date, seed and fruit production has not been observed on plants of the new *Impatiens*.

Pathogen & pest resistance: To date, plants of the new *Impatiens* have not been observed to be resistant to pathogens and pests common to *Impatiens* plants.

Garden performance: Plants of the new *Impatiens* have been observed to have good garden performance and tolerate temperatures ranging from about 5° C. to about 40° C.

It is claimed:

1. A new and distinct *Impatiens* plant named 'Dongipetorsta 21' as illustrated and described.

* * * * *